United States Patent [19]

Hassenrück et al.

[11] Patent Number: 5,208,341
[45] Date of Patent: May 4, 1993

[54] CARBONYLAMINOSTYRYLS

[75] Inventors: Karin Hassenrück, Düsseldorf; Roderich Raue, Leverkusen, both of Fed. Rep. of Germany

[73] Assignee: Bayer Aktiengesellschaft, Leverkusen, Fed. Rep. of Germany

[21] Appl. No.: 771,714

[22] Filed: Oct. 4, 1991

[30] Foreign Application Priority Data

Oct. 11, 1990 [DE] Fed. Rep. of Germany ....... 4032208

[51] Int. Cl.$^5$ .................. C07D 215/12; C07D 215/14
[52] U.S. Cl. .................................................... 546/175
[58] Field of Search ......................................... 546/175

[56]    References Cited
   U.S. PATENT DOCUMENTS 3,346,571  10/1967  Spatz et al. ........................ 548/455
   4,598,150   7/1986  Fujisaki et al. .................... 546/152
   4,820,841   4/1989  Fujisaki et al. .................... 546/152

FOREIGN PATENT DOCUMENTS 0206751  12/1986  European Pat. Off. ............ 546/175

*Primary Examiner*—C. Warren Ivy
*Assistant Examiner*—Zinna N. Davis
*Attorney, Agent, or Firm*—Sprung, Horn, Kramer & Woods

[57]    ABSTRACT

The new carbonylaminostyryls of the formula (I)

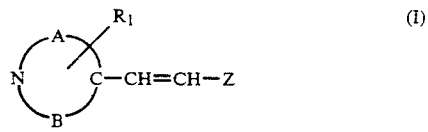

in which the substituents $R_1$, A, B and Z have the meaning given in the description, are especially suitable for the production of recording materials which can be used for pressure-sensitive copying, or of thermoreactive or electrochromic recording materials.

6 Claims, No Drawings

CARBONYLAMINOSTYRYLS

The present invention relates to new carbonylaminostyryls, processes for their preparation and their use in materials for pressure-sensitive copying and thermoreactive or electrochromic recording.

New carbonylaminostyryls of the formula

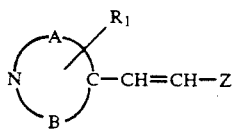

(I)

in which
- A represents the remaining members of an optionally substituted heterocyclic ring system to which a further carbocyclic ring is optionally fused,
- B represents a double bond or the grouping =CH—CH=,
- $R_1$ represents hydrogen, alkyl, alkenyl, cycloalkyl, alkoxy or halogen, and
- Z represents

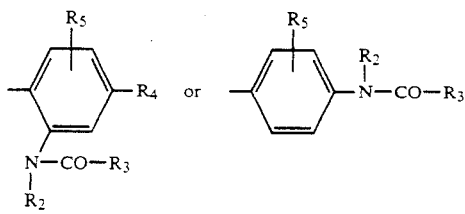

wherein
- $R_2$ represents hydrogen, alkyl, alkenyl, cycloalkyl, aralkyl, aryl or hetaryl,
- $R_3$ represents hydrogen, alkyl, alkenyl, cycloalkyl, aralkyl, aryl, alkoxy, dialkylamino, alkylamino, cycloalkylamino, arylamino, aralkylamino or hetaryl, or
- $R_2$ and $R_3$, together with the nitrogen atom and the carbon atom to which they are bonded, form an optionally substituted 4- to 8-membered ring, or
- $R_2$ and $R_5$, in the case where $R_5$ is in the orthoposition relative to the nitrogen, together with the nitrogen atom and the carbon atom to which they are bonded, form an optionally substituted 5- to 7-membered ring, and
- $R_4$ and $R_5$ independently of one another represent hydrogen, alkyl, alkenyl, cycloalkyl, alkoxy or halogen, have been found.

The heterocyclic system completed by A can be substituted by one or more identical or different radicals $R_1$.

All the abovementioned alkyl, alkenyl, cycloalkyl, alkoxy, (di)alkylamino and cycloalkylamino radicals can be straight-chain or branched and optionally substituted by one or more identical or different substituents. The aralkyl and aralkylamino radicals can be optionally substituted by one or more identical or different substituents both in the straight-chain or branched alkyl part and in the aryl part.

The aryl and hetaryl radicals can be optionally substituted by one or more identical or different substituents.

Alkyl radicals, including those in, for example, alkoxy, alkylamino, dialkylamino or aralkyl, can contain up to 18 carbon atoms and can be substituted, for example, by halogen, alkoxy or cyano.

Alkenyl radicals can contain up to 18 carbon atoms and can be substituted, for example, by alkyl, alkoxy, halogen, cyano or aryl.

Aryl radicals, including those in aralkyl groups, are, for example, phenyl, naphthyl or anthracenyl, which can be substituted, for example, by alkyl, alkoxy, halogen or cyano.

Heterocyclic radicals can be substituted by alkyl, alkoxy, halogen or cyano.

Preferred carbonylaminostyryls of the formula (I) are those in which
- A represents the remaining members of a 5- to 7-membered partially saturated or unsaturated heterocyclic ring system which optionally contains 1 or 2 further hetero atoms from the series comprising oxygen, sulphur and nitrogen and to which a saturated or unsaturated 5- to 7-membered carbocyclic ring is optionally fused,
- B represents a double bond or the grouping =CH—CH=,
- $R_1$ represents hydrogen, alkyl having 1 to 8 carbon atoms, which is optionally substituted by one or more substituents from the group comprising alkoxy having 1 to 6 carbon atoms, cyano, hydroxyl and halogen, or cycloalkyl having 3 to 8 carbon atoms, alkenyl having 2 to 6 carbon atoms, alkoxy having 1 to 6 carbon atoms or halogen, and in Z
- $R_2$ represents hydrogen, alkyl having 1 to 8 carbon atoms, which is optionally substituted by one or more substituents from the group comprising alkoxy having 1 to 6 carbon atoms, hydroxyl, cyano and halogen, or alkenyl having 2 to 6 carbon atoms, cycloalkyl having 3 to 8 carbon atoms, which is optionally substituted by one or more substituents from the group comprising alkyl or alkoxy having in each case 1 to 6 carbon atoms, hydroxyl and halogen, or aryl or aralkyl having 1 to 6 carbon atoms in the alkyl part and in each case 6 to 10 carbon atoms in the aryl part, each of which is optionally substituted in the aryl part by one or more substituents from the group comprising alkyl having 1 to 6 carbon atoms and halogen, or represents a saturated or unsaturated 5- to 7-membered heterocyclic ring which contains 1 to 4 hetero atoms from the series comprising oxygen, sulphur and nitrogen and is optionally substituted by one or more alkyl radicals having 1 to 6 carbon atoms, and to which a further saturated or unsaturated 5- to 6-membered carbocyclic ring is optionally fused,
- $R_3$ represents hydrogen, alkyl or alkoxy having in each case 1 to 18 carbon atoms, each of which is optionally substituted by one or more substituents from the group comprising alkoxy having 1 to 6 carbon atoms, cyano, hydroxyl and halogen, or cycloalkyl having 3 to 8 carbon atoms, which is optionally substituted by one or more substituents from the group comprising alkyl or alkoxy having in each case 1 to 6 carbon atoms, hydroxyl and halogen, or aryl or aralkyl having 1 to 6 carbon atoms in the alkyl part and in each case 6 to 10 carbon atoms in the aryl part, each of which is optionally substituted in the aryl part by one or more substituents from the group comprising alkyl having 1 to 6 carbon atoms and halogen, or alkenyl having 2 to 6 carbon atoms, dialkylamino or alkylamino having in each case 1 to 18 carbon atoms in the particular alkyl parts, cycloalkylamino having 3 to 8 carbon atoms, arylamino or aralkylamino having 1 to 6 carbon atoms in the alkyl part and in each case 6 to 10 carbon atoms in the particular aryl parts, each of which is optionally substituted in the aryl part by one or more substituents from the group comprising alkyl having 1 to 6 carbon atoms and halogen, or represents a saturated or unsaturated 5- to 7-membered heterocyclic ring which contains 1 to 4 hetero atoms, such as oxygen, sulphur or nitrogen, and is optionally substituted by one or more alkyl radicals having 1 to 6 carbon atoms, or $R_2$ and $R_3$, together with the nitrogen atom and the carbon atom to which they are bonded, form a saturated or unsaturated 4- to 8-membered ring, which is optionally substituted by one or more alkyl radicals having 1 to 6 carbon atoms and/or oxo radicals, or $R_2$ and $R_5$, in the case where $R_5$ is in the orthoposition relative to the nitrogen, together with the nitrogen atom and the carbon atom to which they are bonded, form a saturated or unsaturated 5- to 7-membered ring, which is optionally substituted by one or more alkyl radicals having 1 to 6 carbon atoms, and $R_4$ and $R_5$ independently of one another represent hydrogen, alkyl having 1 to 18 carbon atoms, which is optionally substituted by one or more substituents from the group comprising alkoxy having 1 to 6 carbon atoms, cyano, hydroxyl and halogen, or alkenyl having 2 to 6 carbon atoms, cycloalkyl having 3 to 8 carbon atoms, ,which is optionally substituted by one or more substituents from the group comprising alkyl or alkoxy having in each case 1 to 6 carbon atoms, cyano and halogen, or alkoxy having 1 to 18 carbon atoms or halogen.

Particularly preferred carbonylaminostyryls of the formula (I) are those in which A represents the remaining members of a 5- to 6-membered partially saturated or unsaturated heterocyclic ring system which optionally contains 1 or 2 further hetero atoms from the series comprising oxygen, sulphur and nitrogen and to which an unsaturated 6-membered carbocyclic ring is optionally fused, B represents a double bond or the grouping =CH—CH=, $R_1$ represents hydrogen, alkyl having 1 to 6 carbon atoms, which is optionally substituted by 1 to 3 substituents from the group comprising alkoxy having 1 to 4 carbon atoms, cyano, hydroxyl, fluorine, chlorine and bromine, or cycloalkyl having 3 to 7 carbon atoms, alkenyl having 2 to 4 carbon atoms, alkoxy having 1 to 4 carbon atoms, fluorine, chlorine or bromine, and in Z $R_2$ represents hydrogen, alkyl having 1 to 6 carbon atoms, which is optionally substituted by 1 to 3 substituents from the group comprising alkoxy having 1 to 4 carbon atoms, hydroxyl, cyano, fluorine, chlorine and bromine, or alkenyl having 2 to 4 carbon atoms, cycloalkyl having 3 to 7 carbon atoms, which is optionally substituted by 1 to 3 substituents from the group comprising alkoxy or alkyl having in each case 1 to 4 carbon atoms, hydroxyl, fluorine, chlorine and bromine, or phenyl, naphthyl, benzyl or phenethyl, each of which is optionally substituted in the phenyl or naphthyl part by 1 to 3 substituents from the group comprising alkyl having 1 to 4 carbon atoms, fluorine, chlorine and bromine, or represents a saturated or unsaturated 5- or 6-membered heterocyclic ring which contains 1 to 3 hetero atoms from the series comprising oxygen, sulphur and nitrogen and to which a further unsaturated 5 to 6-membered carbocyclic ring is optionally fused, $R_3$ represents hydrogen, alkyl or alkoxy having in each case 1 to 18 carbon atoms, each of which is optionally substituted by 1 to 3 substituents from the group comprising alkoxy having 1 to 4 carbon atoms, cyano, hydroxyl, fluorine, chlorine and bromine, or cycloalkyl having 3 to 7 carbon atoms, which is optionally substituted by 1 to 3 substituents from the group comprising alkyl or alkoxy having in each case 1 to 4 carbon atoms, hydroxyl, fluorine, chlorine and bromine, or phenyl, naphthyl, benzyl or phenethyl, each of which is optionally substituted in the phenyl or naphthyl part by 1 to 3 substituents from the group comprising alkyl having 1 to 4 carbon atoms, fluorine, chlorine and bromine, or alkenyl having 2 to 4 carbon atoms, dialkylamino or alkylamino having in each case 1 to 18 carbon atoms in the particular alkyl parts, cycloalkylamino having 3 to 7 carbon atoms, phenylamino, naphthylamino, benzylamino or phenethylamino, each of which is optionally substituted in the phenyl or naphthyl part by 1 to 3 substituents from the group comprising alkyl having 1 to 4 carbon atoms, fluorine, chlorine and bromine, or represents a saturated or unsaturated 5- to 7-membered heterocyclic ring which contains 1 to 3 hetero atoms from the series comprising oxygen, sulphur and nitrogen and is substituted by 1 to 4 alkyl radicals having 1 to 4 carbon atoms, or $R_2$ and $R_3$, together with the nitrogen atom and the carbon atom to which they are bonded, form a saturated or unsaturated 4- to 8-membered ring which is optionally substituted by 1 to 6 alkyl radicals having 1 to 4 carbon atoms and/or oxo radicals, or $R_2$ and $R_5$, in the case where $R_5$ is in the orthoposition relative to the nitrogen, together with the nitrogen atom and the carbon atom to which they are bonded, form a saturated or unsaturated 5- to 7-membered ring which is optionally substituted by 1 to 3 alkyl radicals having 1 to 4 carbon atoms, and $R_4$ and $R_5$ independently of one another represent hydrogen, alkyl having 1 to 16 carbon atoms, which is optionally substituted by 1 to 3 substituents from the group comprising alkoxy having 1 to 4 carbon atoms, cyano, hydroxyl and halogen, or alkenyl having 2 to 4 carbon atoms, cycloalkyl having 3 to 7 carbon atoms, which is optionally substituted by 1 to 3 substituents from the group comprising alkyl or alkoxy having in each case 1 to 4 carbon atoms, cyano and halogen, or alkoxy having 1 to 16 carbon atoms, fluorine, chlorine or bromine.

Especially preferred carbonylaminostyryls of the formula (I) are those in which

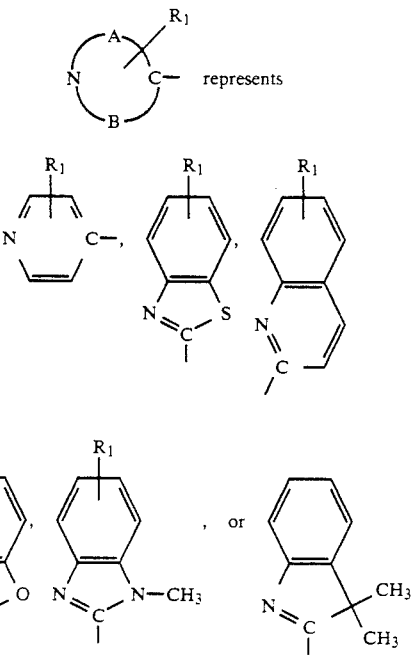 represents

R₁ represents hydrogen, alkyl having 1 to 4 carbon atoms, which is optionally substituted by methoxy, ethoxy, cyano, hydroxyl or chlorine, or cyclopentyl, cyclohexyl, vinyl, allyl, methoxy, ethoxy, n-propoxy or chlorine, and in Z R₂ represents hydrogen, alkyl having 1 to 4 carbon atoms, which is optionally substituted by methoxy, ethoxy, cyano, hydroxyl or chlorine, or cyclopentyl, cyclohexyl, vinyl or allyl; or represents phenyl or benzyl, each of which is optionally substituted in the phenyl part by methyl, methoxy, cyano or chlorine, or represents pyridyl, pyrimidyl, benzimidazolyl, benzoxazolyl, benzothiazolyl or quinolyl, R₃ represents hydrogen, alkyl or alkoxy having in each case 1 to 18 carbon atoms, each of which is optionally substituted by methoxy, ethoxy, cyano, hydroxyl or chlorine; or represents cyclopentyl, cyclohexyl, phenyl, benzyl or naphthyl, each of which is optionally substituted by methyl, methoxy, cyano or chlorine; or represents vinyl or allyl; or dialkylamino or alkylamino having in each case 1 to 18 carbon atoms in the particular alkyl parts, cyclopentylamino, cyclohexylamino or phenylamino, or represents pyridyl, pyrimidyl, thienyl, furyl, pyrrolyl, pyrazinyl, 1-pyrrolidyl or 1-piperidyl, the heterocyclic radicals in each case optionally being substituted by 1 to 4 methyl groups, or R₂ and R₃, together with the nitrogen atom and the carbon atom to which they are bonded, form a 5- or 6-membered saturated or unsaturated ring which is optionally substituted by 1 to 6 methyl radicals and/or oxo radicals, or R₂ and R₅, in the case where R₅ is in the orthoposition relative to the nitrogen, together with the nitrogen atom and the carbon atom to which they are bonded, form a saturated or unsaturated 5- to 6-membered ring which is optionally substituted by 1 to 3 methyl radicals, R₄ represents hydrogen, alkyl having 1 to 14 carbon atoms, which is optionally substituted by methoxy, ethoxy, cyano, hydroxyl or chlorine, or cyclopentyl, cyclohexyl, vinyl, allyl, alkoxy having 1 to 14 carbon atoms or chlorine, and R₅ represents hydrogen, alkyl or alkoxy having in each case 1 to 14 carbon atoms.

Particularly preferred carbonylaminostyryls of the formula (I) are those in which

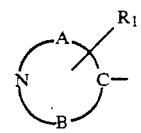

represents

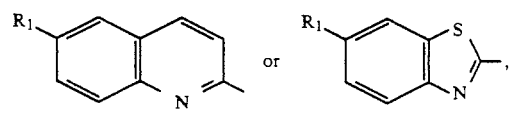

R₁ represents hydrogen, methyl, ethyl, hydroxymethyl, chloromethyl, methoxymethyl, chloroethyl, cyanomethyl, hydroxyethyl, methoxy, ethoxy or chlorine, in Z R₂ represents hydrogen, methyl, ethyl, n-propyl, i-propyl, n-butyl, s-butyl, i-butyl, t-butyl, hydroxymethyl or hydroxyethyl, R₃ represents hydrogen, methyl, ethyl, propyl, hexyl, heptyl, octyl, 2-methylpropyl, nonyl, decyl, dodecyl, hexadecyl, octadecyl, cyclopentyl, cyclohexyl, benzyl, phenyl, methoxy, ethoxy, propoxy, butoxy, pentoxy, hexoxy, heptoxy, octoxy, 2-ethylhexoxy, 1,3-dimethylbutoxy, 1-ethylpropoxy, 3,5,5-trimethylhexoxy, dodecyloxy, hexadecyloxy, octadecyloxy, dimethylamino, diethylamino, dipropylamino, dibutylamino, diisopropylamino, di(2-ethylbutyl)amino, di(2-methylpropyl)amino, 1-methylpropaneamino, 1,1-dimethylethaneamino, octylamino, decylamino, dodecylamino, hexadecylamino, octadecylamino, cyclobutylamino, cyclopentylamino or cyclohexylamino, R₄ represents hydrogen, methyl, ethyl, propyl, butyl, hexyl, methoxy, ethoxy, propoxy, butoxy, hexoxy, octoxy, decyloxy, dodecyloxy or chlorine, and R₅ represents hydrogen, methyl, ethyl, propyl, butyl, hexyl, methoxy, ethoxy, propoxy, butoxy, hexoxy, octoxy, decyloxy or dodecyloxy.

Particularly preferred carbonylaminostyryls are those of the formulae

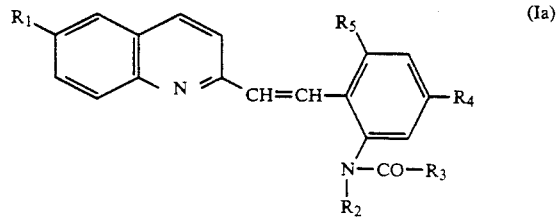

and

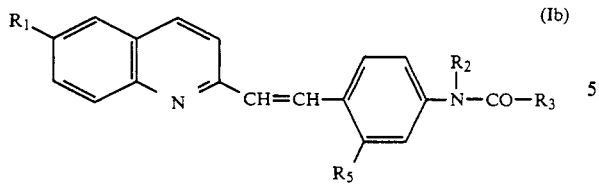

in which
- $R_1$ represents hydrogen, methyl, ethyl, methoxy, ethoxy or chlorine,
- $R_2$ represents hydrogen, methyl, ethyl, n-propyl, i-propyl, n-butyl, sbutyl, i-butyl or t-butyl,
- $R_3$ represents hydrogen, methyl, ethyl, propyl, hexyl, heptyl, octyl, 2-methylpropyl, nonyl, decyl, dodecyl, hexadecyl, octadecyl, cyclopentyl, cyclohexyl, benzyl, phenyl, methoxy, ethoxy, propoxy, butoxy, pentoxy, hexoxy, heptoxy, octoxy, 2-ethylhexoxy, 1,3-dimethylbutoxy, 1-ethylpropoxy, 3,5,5-trimethylhexoxy, dodecyloxy, hexadecyloxy, octadecyloxy, dimethylamino, diethylamino, dipropylamino, dibutylamino, diisopropylamino, di(2-ethylbutyl)amino, di(2-methylpropyl)amino, 1-methylpropaneamino, 1,1-dimethylethaneamino, octylamino, decylamino, dodecylamino, hexadecylamino, octadecylamino, cyclobutylamino, cyclopentylamino or cyclohexylamino,
- $R_4$ represents hydrogen, methyl, ethyl, propyl, butyl, hexyl, methoxy, ethoxy, propoxy, butoxy, hexoxy, octoxy, decyloxy, dodecyloxy or chlorine, and
- $R_5$ represents hydrogen, methyl, ethyl, propyl, butyl, hexyl, methoxy, ethoxy, propoxy, butoxy, hexoxy, octoxy, decyloxy or dodecyloxy.

The new carbonylaminostyryls of the formula (I) can be prepared by a process in which A) compounds of the formula (II)

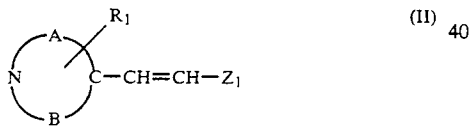

in which
A, B and R have the abovementioned meaning, and

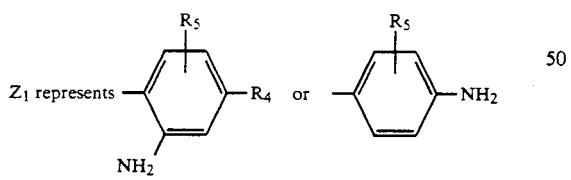

wherein $R_4$ and $R_5$ have the abovementioned meaning, are either a) acylated with compounds of the formula

in which
- Y represents halogen, in particular chlorine or bromine, and
- $R_3'$ represents alkyl, alkenyl, cycloalkyl, aralkyl, aryl or hetaryl, in particular alkyl having to 18 carbon atoms, which is optionally substituted by one or more substituents from the group comprising alkoxy having 1 to 6 carbon atoms, cyano, hydroxyl and halogen, or cycloalkyl having 3 to 8 carbon atoms which is optionally substituted by one or more substituents from the group comprising alkyl or alkoxy having in each case 1 to 6 carbon atoms, hydroxyl and halogen, or aryl or aralkyl having 1 to 6 carbon atoms in the alkyl part and in each case 6 to 10 carbon atoms in the aryl part, each of which is optionally substituted in the aryl part by one or more substituents from the group comprising alkyl having 1 to 6 carbon atoms, hydroxyl and halogen, or alkenyl having 2 to 6 carbon atoms, or represents a saturated or unsaturated 5- to 7-membered heterocyclic ring which contains 1 to 4 hetero atoms, such as oxygen, sulphur or nitrogen, and is optionally substituted by one or more alkyl radicals having 1 to 6 carbon atoms, or b) reacted with chloroformic acid esters to give the compounds of the formula

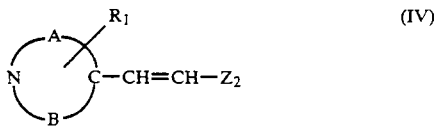

in which

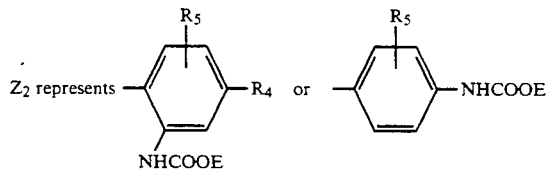

wherein
$R_4$ and $R_5$ have the abovementioned meaning, and E represents methyl, ethyl or phenyl, and A, B and $R_1$ have the abovementioned meaning, and if appropriate the compounds of the formula (IV) thus obtained are further reacted with α) amines of the formula

in which
$R_6$ and $R_7$ are identical or different and in each case represent hydrogen, alkyl, cycloalkyl, aryl or aralkyl, in particular hydrogen, alkyl having 1 to 18 carbon atoms, which is optionally substituted by one or more substituents from the group comprising alkoxy having 1 to 6 carbon atoms, cyano, hydroxyl and halogen, or cycloalkyl having 3 to 8 carbon atoms, which is optionally substituted by one or more substituents from the group comprising alkyl and alkoxy having in each case 1 to 6 carbon atoms, hydroxyl and halogen, or aryl or aralkyl having 1 to 6 carbon atoms in the alkyl part and in each case 6 to 10 carbon atoms in the aryl part, each of which is optionally substituted in the aryl part by one or more substituents from the group comprising alkyl having 1 to 6 carbon atoms and halogen, or β) alcohols of the formula

HO—R$_8$    (VI)

in which

R$_8$ represents alkyl in particular alkyl having 3 to 18 carbon atoms, which is optionally substituted by one or more substituents from the group comprising alkoxy having 1 t 6 carbon atoms, cyano, hydroxyl and halogen, or B) by a process in which compounds of the formula (VII)

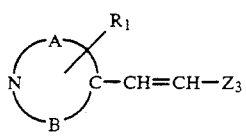
(VII)

in which

A, B and R$_1$ have the above mentioned meaning and Z$_3$ represents

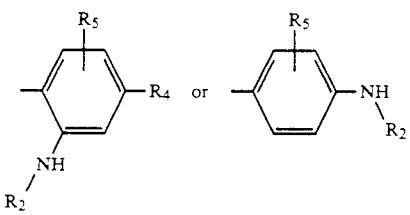

wherein

R$_2$, R$_4$ and R$_5$ have the above mentioned meaning, are either a) reacted with compounds of the formula (III), or b) reacted with ethyl chloroformate to give the corresponding ethoxycarbonylamino-substituted compounds of the formula (I) according to the invention, and if appropriate this compound is further converted by reaction with amines of the formula (V) or alcohols of the formula (VI) as described under (A-b(α)) and (A-b(β)).

The compounds of the formula (II) are also new and the invention likewise relates to these compounds.

The new compounds of the formula (II) can be prepared by a process in which either a) heterocyclic compounds of the formula

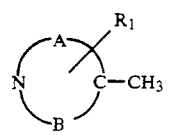
(VIII)

in which

A, B and R$_1$ have the above mentioned meaning, are subjected to a condensation reaction with aldehydes of the formula

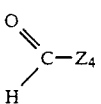
(IX)

in which

Z$_4$ represents

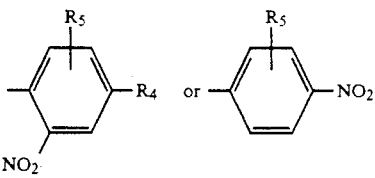

wherein

R$_4$ and R$_5$ have the above mentioned meaning, or with derivatives thereof, such as, for example, anils or hydrazones, if appropriate in the presence of a condensing agent or diluent, such as, for example, acetic acid, acetic anhydride, sulphuryl chloride, thionyl chloride, oxalyl chloride or mixtures of these condensing agents or diluents, at temperatures between, for example, 100° C. and 140° C., and the nitro compounds thus obtained are reduced on the nitro group with a reducing agent, such as, for example, hydrogen in the presence of a platinum catalyst, at temperatures of, for example, 20° C. to 30° C., or b) by a process in which compounds of the formula

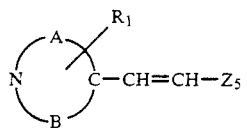
(X)

in which

A, B and R$_1$ have the above mentioned meaning and Z$_5$ represents

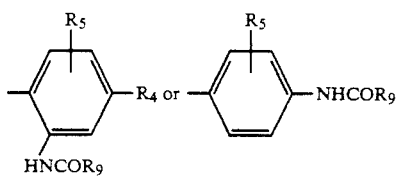

wherein

R$_4$ and R$_5$ have the above mentioned meaning and R$_9$ represents CH$_3$ or C$_2$H$_5$, are hydrolysed, if appropriate in the presence of a solvent, such as methanol, and if appropriate in the presence of an acid, such as hydrochloric acid.

The compounds of the formula (VII) are new and the present invention likewise relates to these compounds.

The new compounds of the formula (VII) can be prepared by a process in which heterocyclic compounds of the formula (VIII) are subjected to a condensation reaction with aldehydes of the formula (XI)

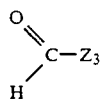

in which

Z₃ has the above mentioned meaning, if appropriate in the presence of a diluent, such as, for example, acetic acid, at temperatures between, for example, 100° and 140° C.

Compounds of the formula (III), amines of the formula (V), alcohols of the formula (VI) and heterocyclic compounds of the formula (VIII) are generally known compounds of organic chemistry.

Processes (A) and (B) according to the invention for the preparation of the new carbonylaminostyryls of the formula (I) are preferably carried out in the presence of diluents. Suitable diluents are, for example, methanol, ethanol and pyridine.

The reaction temperatures can be varied within a relatively wide range in processes (A) and (B) according to the invention. The reactions are in general carried out at temperatures between 80° C. and 150° C., preferably at temperatures between 90° C. and 110° C.

The reactions are carried out and the products are worked up by generally customary methods.

The nitro compounds obtained as intermediate products in the preparation of the new compounds of the formula (II) by a condensation reaction between heterocyclic compounds (VIII) and aldehydes (IX) are in general further reduced without intermediate isolation However, it is also possible for these intermediate products to be isolated by a process in which, for example, the mixture is poured onto water or alcohol when the condensation reaction has ended and the product is precipitated by increasing the pH, for example with alkali metal or alkaline earth metal hydroxides, carbonates or bicarbonates, ammonia or amines.

Suitable heterocyclic compounds (VIII) are, for example, 2-methylbenzothiazole, 2-methylbenzoxazole, 2-methylbenzimidazole, 2-methylquinoline, 4-methylquinoline, 6-chloro-2-methylquinoline, 6-methoxy-2-methylquinoline, 2,3,3-trimethylindolenine, 5-methoxy-2,3,3-trimethylindolenine, 2-methylpyridine and 4-methylpyridine.

Suitable aldehydes (XI) are, for example, 2-aminobenzaldehyde, 5-methyl-2-aminobenzaldehyie, 4-aminobenzaldehyde, 3-methyl-4-aminobenzaldehyie, 2-methoxy-4-aminobenzaldehyde, 3-methoxy-4-aminobenzaldehyde, 2-dodecoxy-4-aminobenzaldehyde, 2-dodecoxy-4-amino-5-methylbenzaldehyde, 2-chloro-4-aminobenzaldehyde, 3-chloro-4-aminobenzaldehyde, N-methyl-4-aminobenzaldehyde, N-ethyl-4-aminobenzaldehyde, N-propyl-4-amino-benzal-dehyde, N-butyl-4-aminobenzaldehyde, N-phenyl-4-aminobenzaldehyde, 2-methyl-4-aminobenzaldehyde, 3-methyl-4-aminobenzaldehyde, 2-ethyl-4-aminobenzaldehyde and 3-ethyl-4-aminobenzaldehyde.

Suitable aldehydes (IX) are, for example, 2-nitro-benzaldehyde, 4-methoxy-2-nitrobenzaldehyde, 5-methyl-4-methoxy-2-nitrobenzaldehyde, 4-nitrobenzaldehyde, 2-methoxy-4-nitrobenzaldehyde, 2-methyl-4-nitrobenzaldehyde, 3-methyl-4-nitrobenzaldehyde, 2-ethoxy-4-nitrobenzaldehyde and 2-dodecoxy-4-nitrobenzaldehyde.

Suitable compounds (III) are, for example, octoyl chloride, decoyl chloride, dodecoyl chloride, benzoyl chloride, 4-methylbenzoyl chloride, 1-naphtholcarbonyl chloride, pyridinecarbonyl chloride, hexanoyl bromide and heptanoyl bromide.

The invention furthermore relates to the use of the chromogenic carbonylaminostyrenes of the formula (I) for recording materials which can be used for pressure-sensitive copying, or thermoreactive or electrochromic recording materials, these recording materials also containing an acid colour developer An individual compound of the formula (I) or mixtures of various compounds of the formula (I), for example mixtures of compounds of the formula. (I) which differ only to the extent that the

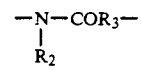

groups in the molecular part Z are in the ortho- and para-position, can be used for such recording materials.

Acid developers which may be mentioned in particular are clays, acid oxides and acid salts, as well as monomeric or polymeric phenols or carboxylic acids.

The colour-forming agents according to the invention can be employed as a mixture with one or more other known colour-forming agents, for example 3,3-bis(aminophenyl)-phthalides, 3,3-bis(indolyl)-phthalides,3-aminofluorans, 1,3-benzoxazines, spirodipyrans, chromenoindoles, phenoxazines, phenothiazines, carbazolylmethanes, 4,4-diaryldihydroquinazolones or other triarylmethane leuco dyestuffs, in particular to produce green, violet, blue or black colorations.

A pressure-sensitive material consists, for example, of at least one pair of sheets which contain at least one colour-forming agent of the formula (I), dissolved or dispersed in a non-volatile organic solvent, and an acid developer.

Such processes and formulations are known, for example, from U.S. Pat. Nos. 2 800 457, 2 800 458, 2 948 753, 3 096 189 and 3 193 404, and from German Offenlegungsschriften (German Published Specifications) 2 555 080 and 2 700 937.

To prevent premature activation of the colour-forming agents present in the pressure-sensitive recording material, the colour-forming agents are preferably enclosed in microcapsules which as a rule can be crushed by pressure.

Suitable capsule materials are, for example, gelatin/gum arabic, polyamides, polyurethanes, polysulphonamides, polyesters, polycarbonate, polysulphonates, polyacrylates and phenol- or urea-formaldehyde condensates, such as are described, for example, in M. Gutcho, Capsule Technology and Microencapsulation, Noyes Data Corporation 1972; G. Baster, Microencapsulation, Processes and Applications, published by J. E. Vandegaar and German Offenlegungsschriften (German Published Specifications) 2 237 545 and 2 119 933.

Microcapsules whose shells consist of polyaddition products of polyisocyanates and polyamides are preferably used in the process according to the invention.

Isocyanates, amines, solvents and a suitable production process for such microcapsules are described, for example, in DE-OS (German Published Specification) 3 203 059.

Thermoreactive recording systems include, for example, heat-sensitive recording and copying materials and papers.

Such a material is described, for example, in German Offenlegungsschrift (German Published Specification) 2 555 080.

Suitable developers are the same electron acceptors as are used in pressure-sensitive papers, preferably phenolic compounds, which are described, for example, in German Patent Specification 1 251 348, and boric acid and organic, preferably aliphatic, dicarboxylic acids.

Another suitable thermoreactive development system is that described in DE-OS (German Published Specification) 3 337 296, in which acid-modified polymers, preferably of acrylonitrile, act as developers.

The compounds according to the invention are superior to the conventional yellow colour developer compounds in the sum of their properties (intensity, migration, untreated paper coloration and light-fastness).

PREPARATION EXAMPLES

Example 1

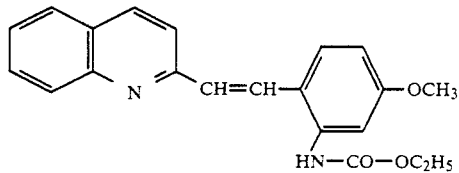

100 g of 4-methoxy-2-nitrobenzaldehyde are suspended in 400 ml of acetic acid, 82 g of quinaldine are added and the mixture is boiled under reflux for 10 hours. The mixture is poured onto 6 l of ice-water and filtered and the residue is dissolved in 1.5 l of methanol. The solution is reduced using a Pt catalyst. The solution is filtered and the filtrate is concentrated. The substance is dissolved in 600 ml of pyridine, and 43 g of ethyl chloroformate are added. The mixture is stirred for 12 hours and poured onto 6 l of water. The substance is taken up in toluene and the mixture is concentrated.

Yield: 60 g, $\lambda_{max}$ (acetic acid)=414 nm.

The product develops with a yellow colour on clay.

Example 2

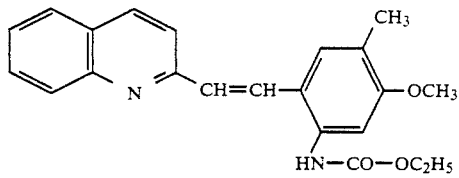

112 g of 5-methyl-4-methoxy-2-ethoxycarbonylaminobenzaldehyde are initially introduced into 300 ml of glacial acetic acid, 71.5 g of quinaldine are added and the mixture is heated under reflux for 3 hours. The mixture is poured onto 5 l of ice-water and rendered alkaline with 50 % strength sodium hydroxide solution. The precipitate is filtered off, washed until neutral and dried in vacuo. Yield: 73 g; $\lambda_{max}$=416 nm (acetic acid).

Example 3

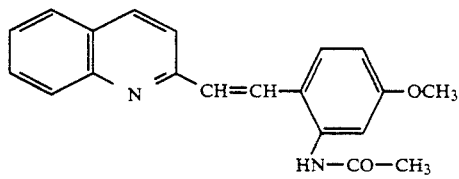

212 g of 4-methoxy-2-aminoanil are suspended in 400 ml of acetic anhydride, 72 g of quinaldine are added and the mixture is boiled under reflux for 8 hours. The mixture is poured onto 5 l of ice-water and filtered and the filtrate is rendered alkaline with 50 % strength sodium hydroxide solution. The residue is filtered off with suction. The product crystallises with a yield of 112 g; $\lambda_{max}$=403 nm (acetic acid).

The compounds of the general formula

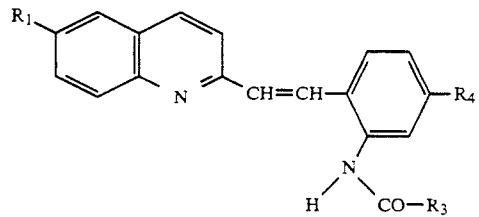

listed in Table 1 were obtained analogously to Examples 1, 2 and 3 and if appropriate by subsequent further reaction with alcohols (VI) or amines (V).

TABLE 1

| Example | $R_1$ | $R_4$ | $R_3$ | $\lambda_{max}$ [nm] |
|---|---|---|---|---|
| 4 | H | OCH$_3$ | OCH$_2$—CH$_2$—CH$_2$—C$_4$H$_9$ | 412 |
| 5 | H | OCH$_3$ | OCH(C$_2$H$_5$)$_2$ | 413 |
| 6 | H | OCH$_3$ | O(CH$_2$)$_2$CH—CH$_2$—C(CH$_3$)$_3$<br>\|<br>CH$_3$ | 412 |
| 7 | H | OCH$_3$ | OC$_{12}$H$_{25}$ | 411 |
| 8 | H | OC$_8$H$_{17}$ | OC$_2$H$_5$ | 410 |
| 9 | H | OC$_{12}$H$_{25}$ | OC$_2$H$_5$ | 411 |
| 10 | Cl | OCH$_3$ | OC$_6$H$_5$ | 439 |
| 11 | Cl | OCH$_3$ | OC$_2$H$_5$ | 441 |
| 12 | Cl | OCH$_3$ | OC$_{12}$H$_{25}$ | 442 |
| 13 | Cl | OC$_{12}$H$_{25}$ | OC$_{12}$H$_{25}$ | 443 |

TABLE 1-continued

| Example | $R_1$ | $R_4$ | $R_3$ | $\lambda_{max}$ [nm] |
|---|---|---|---|---|
| 14 | $OCH_3$ | $OCH_3$ | $OC_{12}H_{25}$ | 420 |
| 15 | H | $OCH_3$ | $-NH-C_{18}H_{37}$ | 431 |
| 16 | H | $OCH_3$ | $-NH-C_{12}H_{25}$ | 429 |
| 17 | H | $OCH_3$ | $-NH-CH(CH_3)C_2H_5$ | 428 |
| 18 | H | $OCH_3$ | $-NH-C(CH_3)_3$ | 427 |
| 19 | H | $OCH_3$ | $-N(C_4H_9)_2$ | 425 |
| 20 | H | $OCH_3$ | $-N(CH_2CH(C_2H_5)_2)_2$ | 426 |
| 21 | H | $OC_{12}H_{25}$ | $-N(CH(CH_3)_2)_2$ | 430 |
| 22 | H | $OCH_3$ | $-N(C_{18}H_{37})CH_3$ | 429 |
| 23 | H | $OCH_3$ | $-N(CH_2CH(CH_3)_2)_2$ | 430 |
| 24 | H | $OC_{12}H_{25}$ | 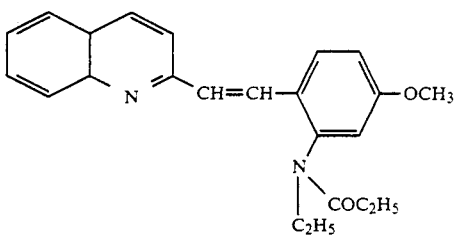 | 428 |

Example 25

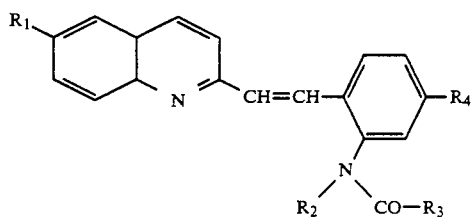

72 g of quinaldine and 75 g of 4-methoxy-2-(N-ethylamino)-benzaldehyde are heated at 100° C. in 30 ml of acetic acid for 8 hours. The mixture is poured onto 3 l of ice-water and rendered alkaline with 50 % strength sodium hydroxide solution at room temperature. The precipitate is filtered off with suction and dried. It is then initially introduced into 300 ml of pyridine, 65 g of ethyl chloroformate are added and the mixture is heated at 80° C. for 2 hours. The mixture is poured onto 600 ml of water and filtered with suction. The product crystallizes with a yield of 75 g, $\lambda_{max}=396$ nm (acetic acid).

The compounds of the general formula listed in Table 2 were prepared analogously to Preparation Example 25 and if appropriate by subsequent further reaction with alcohols (VI) or amines (V).

TABLE 2

| Example | $R_1$ | $R_4$ | $R_2$ | $R_3$ | $\lambda_{max}$ [nm] |
|---|---|---|---|---|---|
| 26 | H | $OCH_3$ | $C_2H_5$ | $OC_6H_5$ | 395 |
| 27 | H | $OCH_3$ | $C_4H_9$ | $OCH_3$ | 397 |
| 28 | H | $OCH_3$ | $C_4H_9$ | $OC_2H_5$ | 398 |
| 29 | H | $OC_8H_{17}$ | $C_2H_5$ | $OC_2H_5$ | 398 |
| 30 | H | $OC_{12}H_{25}$ | $C_4H_9$ | $OC_2H_5$ | 396 |
| 31 | H | $OCH_3$ | $C_2H_5$ | $-N(H)(C_{12}H_{25})$ | 423 |

The compounds of the general formula

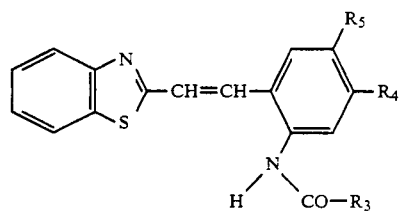

listed in Table 3 were obtained analogously to Preparation Examples 1, 2 and 3 and if appropriate by subsequent further reaction with alcohols (VI) or amines (V).

TABLE 3

| Example | $R_4$ | $R_3$ | $R_5$ | $\lambda_{max}$ [nm] |
|---|---|---|---|---|
| 32 | $OCH_3$ | $OC_{12}H_{25}$ | $CH_3$ | 405 |
| 33 | $OC_{12}H_{25}$ | $OC_{12}H_{25}$ | $CH_3$ | 404 |
| 34 | $OC_{12}H_{25}$ | $OC_{12}H_{25}$ | $CH_3$ | 399 |
| 35 | $OC_{12}H_{25}$ | $OC_2H_5$ | $CH_3$ | 402 |
| 36 | $OCH_3$ | $OC_2H_5$ | $CH_3$ | 403 |
| 37 | $OCH_3$ | $-N(H)(C_{12}H_{25})$ | H | 418 |

Example 38

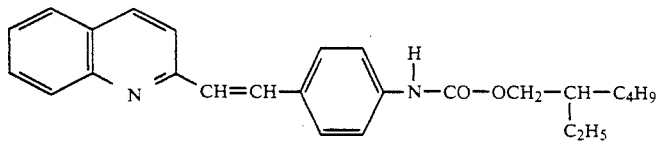

212 g of 4-aminoanil are suspended in 400 ml of acetic anhydride, 72 g of quinaldine are added and the mixture is boiled under reflux for 8 hours. The mixture is poured onto 5 l of ice-water and filtered and the filtrate is rendered alkaline with 50 % strength sodium hydroxide solution. The residue is filtered off with suction and recrystallised from methanol. The product is heated under reflux in 450 ml of methanol, 190 g of 10 % strength hydrochloric acid are added and the mixture is refluxed for 24 hours. The mixture is poured onto 1.5 l of water, rendered alkaline with 50 % strength sodium hydroxide solution and filtered with suction. The dried product is initially introduced into 300 ml of pyridine, 34 g of ethyl chloroformate are added and the mixture is stirred overnight at room temperature. The mixture is poured onto 300 ml of water and filtered with suction. The dried product is heated at 180° C. in 117 g of 2-ethyl-1-hexanol, during which ethanol is distilled off. When the reaction is complete, the mixture is concentrated in vacuo. The product crystallises out with a yield of 63 g. $\lambda_{max}=410$ nm (acetic acid). The product develops with a yellow colour on clay.

Example 39

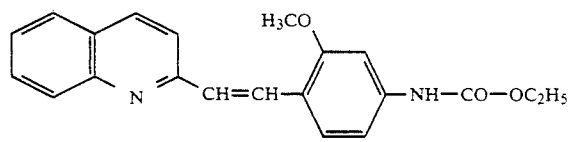

112 g of 2-methoxy-4-ethoxycarbonylaminobenzaldehyde are initially introduced into 300 ml of glacial acetic acid, 71.5 g of quinaldine are added and the mixture is heated under reflux for 3 hours. The mixture is poured onto 5 l of ice-water and rendered alkaline with 50 % strength sodium hydroxide solution. The precipitate is filtered off, washed until neutral and dried in vacuo. Yield: 73 g; $\lambda_{max}=414$ nm (acetic acid).

Example 40

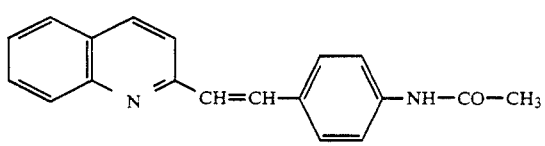

212 g of 4-aminoanil are suspended in 400 ml of acetic anhydride, 72 g of quinaldine are added and the mixture is boiled under reflux for 8 hours. The mixture is poured onto 5 l of ice-water and filtered and the filtrate is rendered alkaline with 50 % strength sodium hydroxide solution. The residue is filtered off with suction. The product crystallises with a yield of 96 g; $\lambda_{max}$ (glacial acetic acid): 401 nm.

The compounds of the general formula

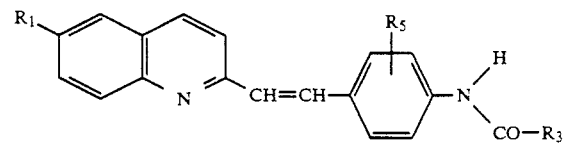

listed in Table 4 were prepared analogously to Preparation Examples 38, 89 and 90 and if appropriate by further derivatisation by means of amines (V) or alcohols (VI).

TABLE 4

| Example | $R_1$ | $R_5$ | $R_3$ | $\lambda_{max}$ [nm] |
|---|---|---|---|---|
| 41 | H | H | $OCH-CH_2-CH-C_4H_9$<br>   \|          \|<br>  $CH_3$      $C_2H_5$ | 411 |
| 42 | H | H | $OCH(C_2H_5)_2$ | 409 |
| 43 | H | H | $O(CH_2)_2CH-CH_2-C(CH_3)_3$<br>              \|<br>              $CH_3$ | 412 |
| 44 | H | H | $OC_{12}H_{25}$ | 410 |
| 45 | H | H | $OC_2H_5$ | 409 |
| 46 | H | H | $OC_6H_5$ | 412 |
| 47 | Cl | H | $OC_6H_5$ | 413 |
| 48 | Cl | H | $OC_2H_5$ | 411 |
| 49 | Cl | H | $OC_{12}H_{25}$ | 412 |
| 50 | H | 2-$OC_{12}H_{25}$ | $OC_2H_5$ | 416 |
| 51 | H | 2-$OCH_3$ | $OC_{12}H_{25}$ | 415 |
| 52 | Cl | 2-$OCH_3$ | $OC_{12}H_{25}$ | 442 |
| 53 | Cl | 2-$OCH_3$ | $OC_2H_5$ | 441 |
| 54 | Cl | 2-$OC_{12}H_{25}$ | $OC_2H_5$ | 442 |
| 55 | H | H | $C_{17}H_{35}$ | 403 |
| 56 | H | H | $C_{17}H_{33}$ | 405 |
| 57 | H | H | $CH_2CH(CH_3)_2$ | 402 |
| 58 | H | H | $C_6H_5$ | 403 |
| 59 | Cl | H | $CH_3$ | 377 |
| 60 | H | H | $-NH-C_{18}H_{37}$ | 425 |
| 61 | H | H | $-NH-C_{12}H_{25}$ | 425 |
| 62 | H | H | $-NH-CH(CH_3)C_2H_5$ | 424 |
| 63 | H | H | $-NH-C(CH_3)_2$ | 424 |
| 64 | H | H | $-N(C_4H_9)_2$ | 419 |
| 65 | H | H | $-N(CH_2CH(C_2H_5)_2)_2$ | 420 |
| 66 | H | H | $-N(CH(CH_3)_2)_2$ | 421 |
| 67 | H | H | $-N(C_{18}H_{37})CH_3$ | 421 |
| 68 | H | H | $-N(CH_2CH(CH_3)_2)_2$ | 420 |
| 69 | H | H | 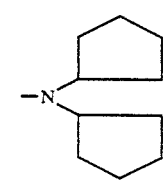 | 420 |
| 70 | Cl | H | $-NH-C_{12}H_{25}$ | 415 |

The compounds of the general formula

TABLE 5

| Example | $R_3$ | $\lambda_{max}$ [nm] |
|---|---|---|
| 71 | $OC_2H_5$ | 358 |
| 72 | $OC_6H_5$ | 360 |
| 73 | $OC_{12}H_{25}$ | 359 |
| 74 | $-NH-C_{12}H_{25}$ | 359 | listed in Table 5 were prepared analogously to Examples 38, 39 and 40 and if appropriate by subsequent further derivatisation with amines (V) or alcohols (VI).

TABLE 5

| Example | $R_3$ | $\lambda_{max}$ [nm] |
|---|---|---|
| 71 | $OC_2H_5$ | 358 |
| 72 | $OC_6H_5$ | 360 |
| 73 | $OC_{12}H_{25}$ | 359 |
| 74 | $-NH-C_{12}H_{25}$ | 359 |

Example 75

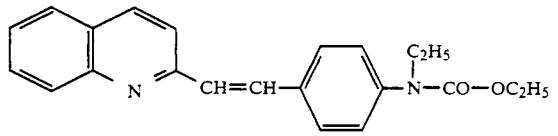

71.5 g of quinaldine and 75 g of 4-(N-ethylamino)-benzyldehyde are heated at 100° C. in 300 ml of acetic acid for 7 hours. The mixture is poured onto 3 l of ice-water and rendered alkaline with 50 % strength sodium hydroxide solution at room temperature. The precipitate is filtered off with suction and dried. The product is initially introduced into 300 ml of pyridine, 65 g of ethyl chloroformate are added and the mixture is heated at 80° C. for 2 hours. The mixture is poured onto 600 ml of water and filtered with suction. The product crystallises with a yield of 82 g; $\lambda_{max} = 383$ nm (acetic acid).

The compounds of the general formula

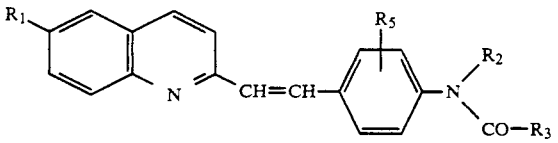

listed in Table 6 were prepared analogously to Example 75 and if appropriate by further reaction with amines (V) or alcohols (VI).

TABLE 6

| Example | $R_1$ | $R_5$ | $R_2$ | $R_3$ | $\lambda_{max}$ [nm] |
|---|---|---|---|---|---|
| 76 | H | H | $C_2H_5$ | $OC_6H_5$ | 389 |
| 77 | H | H | $C_2H_5$ | $OC_2H_5$ | 384 |
| 78 | H | 2-$CH_3$ | $C_4H_9$ | $OC_2H_5$ | 392 |
| 79 | H | 3-$CH_3$ | $C_2H_5$ | $OC_2H_5$ | 390 |
| 80 | H | H | $C_4H_9$ | $OC_2H_5$ | 391 |

What is claimed is:
1. Carbonylaminostyryls of the formula

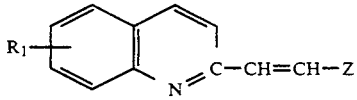

wherein $R_1$ represents hydrogen, alkyl having 1 to 8 carbon atoms, which is optionally substituted by one or more substituents selected from the group consisting of alkoxy having 1 to 6 carbon atoms, cyano, hydroxyl and halogen, or represents cycloalkyl having 3 to 8 carbon atoms, alkenyl having 2 to 6 carbon atoms, alkoxy having 1 to 6 carbon atoms or halogen, and represents

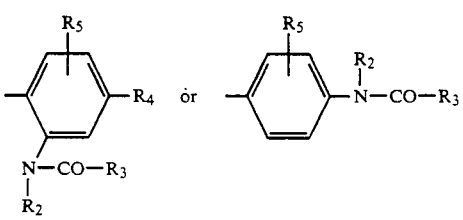

wherein $R_2$ represents hydrogen, alkyl having 1 to 8 carbon atoms, which is optionally substituted by one or more substituents selected from the group consisting of alkoxy having 1 to 6 carbon atoms, hydroxyl, cyano and halogen, or represents alkenyl having 2 to 6 carbon atoms, cyclo-alkyl having 3 to 8 carbon atoms, which is optionally substituted by one or more substituents selected from the group consisting of alkyl, alkoxy having in each case 1 to 6 carbon atoms, hydroxyl and halogen, or represents aryl or aralkyl having 1 to 6 carbon atoms in the alkyl part and in each case 6 to 10 carbon atoms in the aryl part, each of which is optionally substituted in the aryl part by one or more substituents selected from the group consisting of alkyl having 1 to 6 carbon atoms and halogen, $R_3$ represents hydrogen, alkyl or alkoxy having in each case 1 to 18 carbon atoms, each of which is optionally substituted by one or more substituents selected from the group consisting of alkoxy having 1 to 6 carbon atoms, cyano, hydroxyl and halogen, or represents cycloalkyl having 3 to 8 carbon atoms, which is optionally substituted by one or more substituents selected from the group consisting of alkyl, alkoxy having in each case 1 to 6 carbon atoms, hydroxyl and halogen, or represents aryl or aralkyl having 1 to 6 carbon atoms in the alkyl part and in each case 6 to 10 carbon atoms in the aryl part, each of which is optionally substituted in the aryl part by one or more substituents selected from the group comprising alkyl having 1 to 6 carbon atoms and halogen, or represents alkenyl having 2 to 6 carbon atoms, dialkylamino or alkylamino having in each case 1 to 18 carbon atoms in the alkyl part, cycloalkylamino having 3 to 8 carbon atoms, arylamino or aralkyl-amino having 1 to 6 carbon atoms in the alkyl part and in each case 6 to 10 carbon atoms in the aryl part, each of which is optionally substituted in the aryl part by one or more substituents selected from the group consisting of alkyl having 1 to 6 carbon atoms and halogen, and R$_4$ and R$_5$ independently of one another represent hydrogen, alkyl having 1 to 18 carbon atoms, which is optionally substituted by one or more substituents selected from the group consisting of alkoxy having 1 to 6 carbon atoms, cyano, hydroxyl and halogen, or represents alkenyl having 2 to 6 carbon atoms, cycloalkyl having 3 to 8 carbon atoms, which is optionally substituted by one or more substituents selected from the group consisting of alkyl, alkoxy having in each case 1 to 6 carbon atoms, cyano and halogen, or represents alkoxy having 1 to 18 carbon atoms or halogen.

2. Carbonylaminostyryls of claim 1, wherein

R$_1$ represents hydrogen, alkyl having 1 to 6 carbon atoms,which is optionally substituted by 1 to 3 substituents selected from the group consisting of alkoxy having 1 to 4 carbon atoms, cyano, hydroxyl, fluorine, chlorine and bromine, or represents cycloalkyl having 3 to 7 carbon atoms, alkenyl having 2 to 4 carbon atoms, alkoxy having 1 to 4 carbon atoms, fluorine, chlorine or bromine, and in Z R$_2$ represents hydrogen, alkyl having 1 to 6 carbon atoms, which is optionally substituted by 1 to 3 substituents selected from the group consisting of alkoxy having 1 to 4 carbon atoms, hydroxyl, cyano, fluorine, chlorine and bromine, or represents alkenyl having 2 to 4 carbon atoms, cycloalkyl having 3 to 7 carbon atoms, which is optionally substituted by 1 to 3 substituents selected from the group consisting of alkoxy or alkyl having in each case 1 to 4 carbon atoms, hydroxyl, fluorine, chlorine and bromine, or represents phenyl, naphthyl, benzyl or phenethyl, each of which is optionally substituted in the phenyl or naphthyl part by 1 to 3 substituents selected from the group consisting of alkyl having 1 to 4 carbon atoms, fluorine, chlorine and bromine, R$_3$ represents hydrogen, alkyl or alkoxy having in each case 1 to 18 carbon atoms, each of which is optionally substituted by 1 to 3 substituents selected from the group consisting of alkoxy having 1 to 4 carbon atoms, cyano, hydroxyl, fluorine, chlorine and bromine, or represents cycloalkyl having 3 to 7 carbon atoms, which is optionally substituted by 1 to 3 substituents selected from the group consisting of alkyl, alkoxy having in each case 1 to 4 carbon atoms, hydroxyl, fluorine, chlorine and bromine, or represents phenyl, naphthyl, benzyl or phenethyl, each of which is optionally substituted in the phenyl or naphthyl part by 1 to 3 substituents selected from the group consisting of alkyl having 1 to 4 carbon atoms, fluorine, chlorine and bromine, or represents alkenyl having 2 to 4 carbon atoms, dialkylamino or alkylamino having in each case 1 to 18 carbon atoms in the alkyl part, cycloalkylamino having 3 to 7 carbon atoms, phenylamino, napthyl-amino, benzylamino or phenethylamino, each of which is optionally substituted in the phenyl or naphthyl part by 1 to 3 substituents selected from the group consisting of alkyl having 1 to 4 carbon atoms, fluorine, chlorine and bromine, and R$_4$ and R$_5$ independently of one another represent hydrogen, alkyl having 1 to 16 carbon atoms, which is optionally substituted by 1 to 3 substituents selected from the group consisting of alkoxy having 1 to 4 carbon atoms, cyano, hydroxyl and halogen, or represents alkenyl having 2 to carbon atoms, cycloalkyl having 3 to 7 carbon atoms, which is optionally substituted by 1 to 3 substituents selected from the group consisting of alkyl, alkoxy having in each case 1 to 4 carbon atoms, cyano and halogen, or represents alkoxy having 1 to 16 carbon atoms, fluorine, chlorine or bromine.

3. Carbonylaminostyryls of claim 1, wherein

R$_1$ represents hydrogen, alkyl having 1 to 4 carbon atoms,which is optionally substituted by methoxy, ethoxy, cyano, hydroxyl or chlorine, cyclopentyl, cyclohexyl, vinyl, allyl, methoxy, ethoxy, n-propoxy or chlorine, and in Z R$_2$ represents hydrogen, alkyl having 1 to 4 carbon atoms, which is optionally substituted by methoxy, ethoxy, cyano, hydroxyl or chlorine, or cyclopentyl, cyclohexyl, vinyl or allyl; or represents phenyl or benzyl, each of which is optionally substituted in the phenyl part by methyl, methoxy, cyano or chlorine, R$_3$ represents hydrogen, alkyl or alkoxy having in each case 1 to 18 carbon atoms, each of which is optionally substituted by methoxy, ethoxy, cyano, hydroxyl or chlorine; or represents cyclopentyl, cyclohexyl, phenyl, benzyl or naphthyl, each of which is optionally substituted by methyl, methoxy, cyano or chlorine; or represents vinyl or allyl; or dialkylamino or alkylamino having in each case 1 to 18 carbon atoms in the alkyl part, cyclopentylamino, cyclohexylamino or phenylamino, R$_4$ represents hydrogen, alkyl having 1 to 14 carbon atoms, which is optionally substituted by methoxy, ethoxy, cyano, hydroxyl or chlorine, or cyclopentyl, cyclohexyl, vinyl, allyl, alkoxy having 1 to 14 carbon atoms or chlorine, and R$_5$ represents hydrogen, alkyl or alkoxy having in each case 1 to 14 carbon atoms.

4. Carbonylaminostyryls of claim 1, wherein

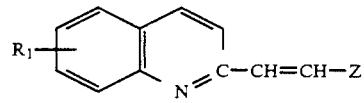

R$_1$ represents hydrogen, methyl, ethyl, hydroxymethyl, chloromethyl, methoxymethyl, chloroethyl, cyanomethyl, hydroxyethyl, methoxy, ethoxy or chlorine, in Z R$_2$ represents hydrogen, methyl, ethyl, n-propyl, i-propyl, n-butyl, s-butyl, i-butyl, t-butyl, hydroxymethyl or hydroxyethyl, R$_3$ represents hydrogen, methyl, ethyl, propyl, hexyl, heptyl, octyl, 2-methylpropyl, nonyl, decyl, dodecyl, hexadecyl, octadecyl, cyclopentyl, cyclohexyl, benzyl, phenyl, methoxy, ethoxy, propoxy, butoxy, pentoxy, hexoxy, heptoxy, octoxy, 2-ethylhexoxy, 1,3-dimethylbutoxy, 1-ethylpropoxy, 3,5,5-trimethylhexoxy, dodecyloxy, hexadecyloxy, octadecyloxy, dimethylamino, diethylamino, dipropylamino, dibutylamino, diisopropylamino, di(2-ethylbutyl)amino, di(2-methylpropyl)amino, 1-methylpropaneamino, 1,1-dimethylethaneamino, octylamino, decylamino, dodecylamino, hexadecylamino, octadecylamino, cyclobutylamino, cyclopentylamino or cyclohexylamino, $R_4$ represents hydrogen, methyl, ethyl, propyl, butyl, hexyl, methoxy, ethoxy, propoxy, butoxy, hexoxy, octoxy, decyloxy, dodecyloxy or chlorine, and $R_5$ represents hydrogen, methyl, ethyl, propyl, butyl, hexyl, methoxy, ethoxy, propoxy, butoxy, hexoxy, octoxy, decyloxy or dodecyloxy.

5. Carbonylaminostyryls of claim 1, of the formula

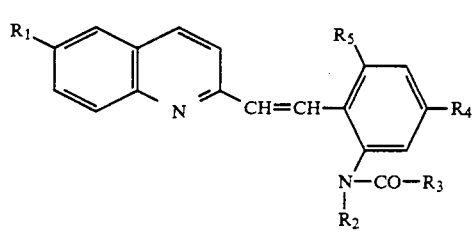

(Ia)

in which $R_1$ represents hydrogen, methyl, ethyl, methoxy, ethoxy or chlorine, $R_2$ represents hydrogen, methyl, ethyl, n-propyl, i-propyl, n-butyl, s-butyl, i-butyl or t-butyl, $R_3$ represents hydrogen, methyl, ethyl, propyl, hexyl, heptyl, octyl, 2-methylpropyl, nonyl, decyl, dodecyl, hexadecyl, octadecyl, cyclopentyl, cyclohexyl, benzyl, phenyl, methoxy, ethoxy, propoxy, butoxy, pentoxy, hexoxy, heptoxy, octoxy, 2-ethylhexoxy, 1,3-dimethylbutoxy, 1-ethylpropoxy, 3,5,5-trimethylhexoxy, dodecyloxy, hexadecyloxy, octadecyloxy, dimethylamino, diethylamino, dipropylamino, dibutylamino, diisopropylamino, di(2-ethylbutyl)amino, di(2-methylpropyl)amino, 1-methylpropaneamino, 1,1-dimethylethaneamino, octylamino, decylamino, dodecylamino, hexadecylamino, octadecylamino, cyclobutylamino, cyclopentylamino or cyclohexylamino, $R_4$ represents hydrogen, methyl, ethyl, propyl, butyl, hexyl, methoxy, ethoxy, propoxy, butoxy, hexoxy, octoxy, decyloxy, dodecyloxy or chlorine, and $R_5$ represents hydrogen, methyl, ethyl, propyl, butyl, hexyl, methoxy, ethoxy, propoxy, butoxy, hexoxy, octoxy, decyloxy or dodecyloxy.

6. Carbonylaminostyryls of claim 1, of the formula

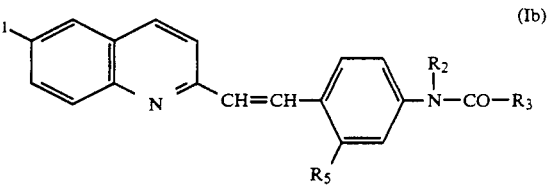

(Ib)

in which $R_1$ represents hydrogen, methyl, ethyl, methoxy, ethoxy or chlorine, $R_2$ represents hydrogen, methyl, ethyl, n-propyl, i-propyl, n-butyl, s-butyl, i-butyl or t-butyl $R_3$ represents hydrogen, methyl, ethyl, propyl, hexyl, heptyl, octyl, 2-methylpropyl, nonyl, decyl, dodecyl, hexadecyl, octadecyl, cyclopentyl, cyclohexyl, benzyl, phenyl, methoxy, ethoxy, propoxy, butoxy, pentoxy, hexoxy, heptoxy, octoxy, 2-ethylhexoxy, 1,3-dimethylbutoxy, 1-ethylpropoxy, 3,5,5-trimethylhexoxy, dodecyloxy, hexadecyloxy, octadecyloxy, dimethylamino, diethylamino, dipropylamino, dibutylamino, diisopropylamino, di(2-ethylbutyl)amino, di(2-methylpropyl)amino, 1-methylpropaneamino, 1,1-dimethylethaneamino, octylamino, decylamino, dodecylamino, hexadecylamino, octadecylamino, cyclobutylamino, cyclopentylamino or cyclohexylamino and $R_5$ represents hydrogen, methyl, ethyl, propyl, butyl, hexyl, methoxy, ethoxy, propoxy, butoxy, hexoxy, octoxy, decyloxy or dodecyloxy.

* * * * *

UNITED STATES PATENT AND TRADEMARK OFFICE
CERTIFICATE OF CORRECTION

PATENT NO. : 5,208,341

DATED : May 4, 1993

INVENTOR(S) : Hassenruck, et al.

It is certified that error appears in the above-identified patent and that said Letters Patent is hereby corrected as shown below:

Col. 20, line 17    Before " represents " insert -- Z --

Col. 22, line 3     Before " carbon " insert -- 4 --

Signed and Sealed this

Twenty-seventh Day of September, 1994

Attest:

BRUCE LEHMAN

*Attesting Officer*    *Commissioner of Patents and Trademarks*